US008802870B2

(12) United States Patent
Gonzalez et al.

(10) Patent No.: US 8,802,870 B2
(45) Date of Patent: Aug. 12, 2014

(54) METHOD FOR CONVERTING TRANS-CIS NEPETALACTONE TO CIS-TRANS NEPETALACTONE USING MOLECULAR SIEVES

(75) Inventors: Yamaira Gonzalez, Wilmington, DE (US); David Richard Corbin, West Chester, PA (US)

(73) Assignee: E I du Pont de Nemours and Company, Wilmington, DE (US)

( * ) Notice: Subject to any disclaimer, the term of this patent is extended or adjusted under 35 U.S.C. 154(b) by 529 days.

(21) Appl. No.: 12/744,513

(22) PCT Filed: Nov. 26, 2008

(86) PCT No.: PCT/US2008/084795
§ 371 (c)(1),
(2), (4) Date: Oct. 15, 2013

(87) PCT Pub. No.: WO2009/070641
PCT Pub. Date: Jun. 4, 2009

(65) Prior Publication Data
US 2010/0261915 A1    Oct. 14, 2010

Related U.S. Application Data

(60) Provisional application No. 60/990,117, filed on Nov. 26, 2007.

(51) Int. Cl.
C07D 311/02    (2006.01)
C07D 309/00    (2006.01)
C07D 311/94    (2006.01)

(52) U.S. Cl.
CPC ..................................... *C07D 311/94* (2013.01)
USPC .......................................... 549/283; 549/273

(58) Field of Classification Search
USPC ................................................. 549/273, 283
See application file for complete search history.

(56) References Cited

U.S. PATENT DOCUMENTS

| | | | |
|---|---|---|---|
| 4,496,467 A | 1/1985 | Munteanu |
| 4,869,896 A | 9/1989 | Coulston |
| 6,462,015 B1 | 10/2002 | Weiss |
| 6,524,605 B1 | 2/2003 | Coats |
| 6,673,756 B2 | 1/2004 | Sonnenberg |
| 7,067,677 B2 | 6/2006 | Manzer |
| 7,232,844 B2 | 6/2007 | Hallahan |
| 7,820,145 B2 | 10/2010 | Tamarkin |
| 2004/0024054 A1 | 2/2004 | Haenke |
| 2005/0244441 A1 | 11/2005 | Courtois |
| 2006/0223878 A1 | 10/2006 | Scialdone |
| 2007/0077262 A1 | 4/2007 | Scialdone |
| 2007/0264297 A1 | 11/2007 | Scialdone |
| 2008/0305135 A1 | 12/2008 | Kroepke |
| 2010/0034906 A1 | 2/2010 | Gonzalez |
| 2010/0092404 A1 | 4/2010 | Hutchenson |
| 2010/0145077 A1 | 6/2010 | Jackson |
| 2010/0145078 A1 | 6/2010 | Fisher |
| 2010/0168447 A1 | 7/2010 | Hutchenson |
| 2010/0261915 A1 | 10/2010 | Gonzalez |

FOREIGN PATENT DOCUMENTS

| | | |
|---|---|---|
| EP | 158976 A2 | 10/1985 |
| EP | 158349 B1 | 3/1990 |
| EP | 159624 B1 | 12/1991 |
| WO | 03/079786 A1 | 10/2003 |

OTHER PUBLICATIONS

International Search Report, PCT/US2008/084795, Dated Nov. 26, 2008.
Libikas et al, Simplified Isolation Procedure and Interconversion of the Diastereomers of Nepetalactone and Nepetalactol, J. Nat. Prod., Vol. 68, 2005, pp. 886-890, XP002519342.
Sakan et al, "The exact nature of matatabilactone and the Terpenes of Nepeta Cataria", Tetrahedron Letters, No. 46, pp. 4097-4102; 1965.
Regnier et al, "Studies on the Composition of the Essential Oils of Three Nepeta Species", Phytochemistry 1967, Vol. 6, pp. 1281 to 1289.
Tanimori et. al., Total Synthesis of (+) Dihydronepetalactone, Agric. Biol. Chem., 1991, vol. 55:1181-11832.
Fleming et. al., Sterocontrol in Organic Synthesis Using Silicon-Containing Compounds, a Synthesis of (+) Dihydronepetalactone Using the SE2 Reaction of an Allysilane, J. Chem. Soc., Perkin Trans, 1998, vol. 1:2645-2649.
Wolinsky et. al., Syntheses of the Dihydronepetalactones, J. Org. Chem., 1972, vol. 37:3376-3378.
Jefson et. al., Chemical Defense of a Rove Bettle, Journal of Chemical Ecology, 1983, vol. 9:150-180.
G.W.K. Cavill et. al., Defensive and Other Secretions of the Australlian Cocktail Ant, Iridomyrex Nitidiceps, Tetrahedron, 1982, vol. 38:1931-1938.
Chris Peterson et. al., Insect Repellents—Past, Present and Future, Pesticide Outlook, Aug. 2001.
Depooter et. al., The Essential Oils Five Nepeta Species. A Preliminary Evaluation of Their Use in Chemotaxonomy by Cluster Analysis, Flavour and Fragrance Journal, 1988, vol. 3:155-159.
Handjieva et. al., Constituents of Essential Oils From Nepeta Cataria L., N. Grandiflora M.B. and N. Nuda L., J. Essential Oil Res., 1996, vol. 8:639-643.
Regnier et al, Nepetalactone and Eipnepetalactone From Nepeta Cataria L., Phytochemistry, 1967, vol. 6:1271-1280.
T. Eisner, Science, 1964, vol. 146:1318-1320.

*Primary Examiner* — Nizal Chandrakumar

(57) ABSTRACT

A method for converting trans-cis nepetalactone to cis-trans nepetalactone using molecular sieves. The molecular sieves may, for example, have a pH in water of at least about 9, and/or may be activated prior to use by heating.

20 Claims, 9 Drawing Sheets

US 8,802,870 B2

METHOD FOR CONVERTING TRANS-CIS NEPETALACTONE TO CIS-TRANS NEPETALACTONE USING MOLECULAR SIEVES

This application claims priority under 35 U.S.C. §119(e) from, and claims the benefit of, U.S. Provisional Application No. 60/990,117, filed Nov. 26, 2007, which is by this reference incorporated in its entirety as a part hereof for all purposes.

TECHNICAL FIELD

This invention relates to a method for converting trans-cis nepetalactone to cis-trans nepetalactone.

BACKGROUND

Dihydronepetalactone ("DHN") is a useful chemical that has been shown to have a variety of properties such as insect repellency [see, for example, Jefson et al (*J. Chemical Ecology* [1983] 9:159-180), or WO 03/79786 (Hallahan)]. Dihydronepetalactone can be produced by contacting purified nepetalactones, or mixtures comprising various nepetalactones, with hydrogen in the presence of a catalyst, as described for example by Regnier et al [*Phytochemistry* (1967) 6:1281-1289]; Waller and Johnson [*Proc. Oklahoma Acad. Sci.* (1984) 64:49-56]; and U.S. Pat. No. 7,067,677 (Manzer).

Catmint oil, which contains a mixture of stereoisomers of nepetalactone (including trans-cis nepetalactone and cis-trans nepetalactone), can be used as a source of nepetalactone for the hydrogenation reaction described above. The hydrogenation of trans-cis nepetalactone at high temperatures may, however, lead to the formation of undesired end-products such as puleganic acid. It is thus desirable to perform the hydrogenation reaction primarily on the cis-trans isomer, and preferably on the cis-trans isomer alone.

U.S. Ser. No. 06/121,134 describes a method for the separation of ZE-nepetalactone and EZ-nepetalactone from catnip oil by dissolving the catnip oil in at least one water-immiscible, non-halogenated solvent, and mixing this solution with an aqueous solution comprising at least one inorganic base. In the presence of the aqueous base, the ZE-nepetalactone is hydrolyzed to ZE-nepetalic acid. The aqueous phase containing ZE-nepetalic acid may be separated from the organic phase containing EZ-nepetalactone. The aqueous phase, optionally, can further be acidified and added to at least one organic solvent to lactonize the ZE-nepetalic acid, in the presence for example of p-toluene sulfonic acid, to ZE-nepetalactone. Thus, this approach requires the hydrolysis of ZE-nepetalactone, and may involve the regeneration of ZE-nepetalactone from ZE-nepetalic acid.

Alternatively, Libikas et al [*J. Nat. Prod.* (2005) 68:886-890] used the base 1,8-diaza-bicyclo[5.4.0]undec-7-ene to convert a trans-cis nepetalactone to cis-trans nepetalactone in refluxing xylene, followed by separation using liquid chromatography. Sakan et al [*Tetrahedron Letters* (1965) 6:4097-4102] have also transformed trans-cis isonepetalactone to nepetalactone by heating with potassium carbonate ($K_2CO_3$) in xylene. Approaches such as the foregoing rely on the use of a solvent such as xylene.

A need thus remains for a method for converting trans-cis nepetalactone to cis-trans nepetalactone that has a minimum of steps, and eliminates steps such as the addition of a co-solvent or the use of an extraction or regeneration step.

SUMMARY

In one embodiment, this invention is related to a method for converting trans-cis nepetalactone to cis-trans nepetalactone by contacting a trans-cis nepetalactone compound, or a mixture comprising trans-cis nepetalactone and cis-trans nepetalactone, with at least one molecular sieve.

In another embodiment, this invention is related to the preparation of dihydronepetalactone or hydrogenated catmint oil after a trans-cis nepetalactone compound, or a mixture comprising trans-cis nepetalactone and cis-trans nepetalactone, has been contacted with at least one molecular sieve.

DETAILED DESCRIPTION

Figure 1:
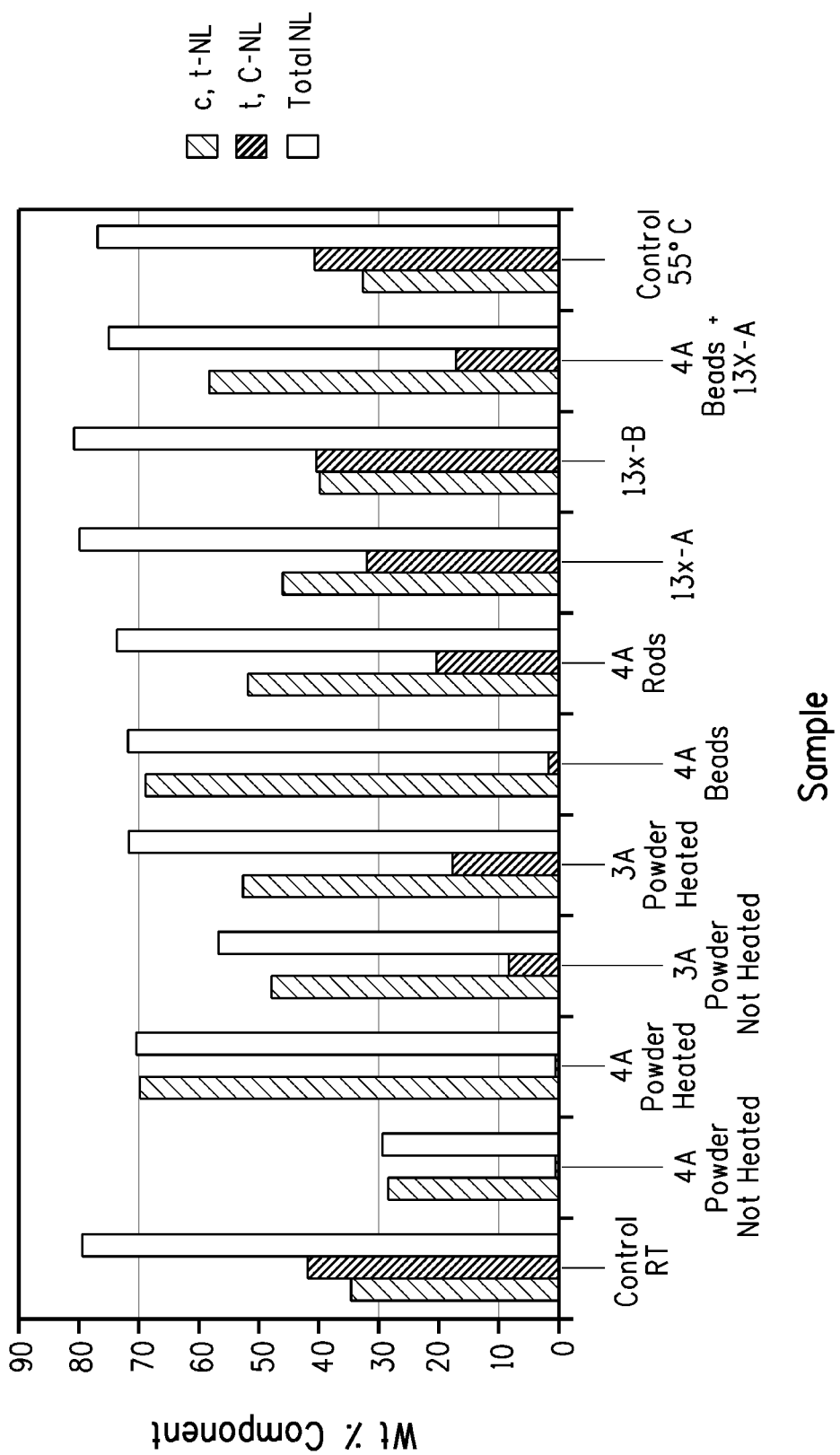
FIG. 1 shows the distribution of the trans-cis and cis-trans nepetalactone isomers after incubating catmint oil with molecular sieves.

This invention relates to a method for converting trans-cis nepetalactone to cis-trans nepetalactone through the use of molecular sieves. To effect the conversion, trans-cis nepetalactone, or a mixture of trans-cis nepetalactone and cis-trans nepetalactone (a "T,C/C,T mixture"), is contacted with at least one molecular sieve, optionally with heating. The trans-cis nepetalactone, or the T,C/C,T mixture, may, for example, be obtained from, or contained in, catmint oil, which may in turn be obtained from the *Nepeta cataria* plant. Trans-cis nepetalactone as treated herein, or the treated mixture, or the treated catmint oil, obtained from the conversion operation is useful for the production of dihydronepetalactone.

The term "nepetalactone" as used herein refers to a compound having the formula:

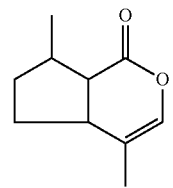

Four stereoisomers of nepetalactone are known to exist in nature. Three isomers commonly found in catmint oil are the cis-trans, trans-cis, and cis-cis isomers, as shown below.

Cis-trans nepetalactone is a compound having the formula:

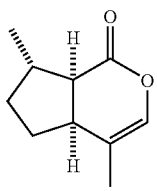

Trans-cis nepetalactone is a compound having the formula:

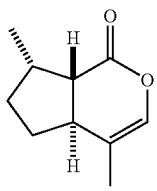

Cis-cis nepetalactone is a compound having the formula:

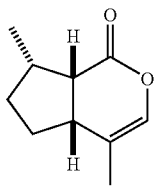

Trans-cis nepetalactone, or a T,C/C,T mixture, as used in the method of this invention may be obtained from, or contained in, catmint oil, which may in turn be obtained from the catmint plant, *Nepeta cataria*. Catmint oil may be obtained from *Nepeta cataria* plants by various isolation processes, including but not limited to steam distillation, organic solvent extraction, microwave-assisted organic solvent extraction, supercritical fluid extraction, mechanical extraction and enfleurage (initial cold extraction into fats followed by organic solvent extraction). The oil can be used in the crude form, or the nepetalactones themselves can be further purified from the oil by distillation, as described for example in U.S. Provisional Application No. 60/876,569, which is by this reference incorporated in its entirety as a part hereof for all purposes.

Catmint oil typically includes more than one nepetalactone isomer, and, as shown in Table 1 below, the concentrations of the isomers can vary based on the source of the plant material and/or the method of catmint oil preparation. This invention is applicable to catmint oils that contain trans-cis nepetalactone at a variety of different levels of content, such as concentrations greater than about 1%, and more particularly greater than about 10%, 15%, 25% or 40%, by weight relative to the total weight of nepetalactone in the oil.

This invention is also applicable, however, to a mixture of trans-cis nepetalactone and cis-trans nepetalactone that is not contained in catmint oil, and in such a mixture trans-cis nepetalactone may be present at a similar variety of different levels of content, such as concentrations greater than about 1%, and more particularly greater than about 10%, 15%, 25% or 40%, by weight relative to the total weight of the mixture.

When trans-cis nepetalactone is present in a mixture with cis-trans nepetalactone at extremely low levels, the trans-cis nepetalactone may be regarded essentially as an impurity in a cis-trans nepetalactone compound. In yet other embodiments, the invention is also applicable to the conversion of a trans-cis nepetalactone compound itself to cis-trans nepetalactone through the use of molecular sieves.

Molecular sieves suitable for use in the method hereof may in general include a natural or synthetic material with a microporous, typically crystalline structure, with pore sizes typically ranging from 5 to 10 Angstroms, that can separate components of a mixture based on molecular size and shape differences. Molecular sieves are three-dimensional crystalline or non-crystalline networks. Although these networks typically comprise oxide lattices containing tetrahedral $Si^{4+}$ and $Al^{3+}$ cations (which compositionally define a zeolite molecular sieve such as described below), other cations can also occupy these sites.

These cations need not occupy exclusively tetrahedral sites in the framework, but must occupy framework and not ion-exchangeable sites. In a molecular sieve, coordination may be tetrahedral, trigonal, trigonal bypyramidal or octahedral, as well as distorted variations of these. More than one type of coordination may occur within the same framework.

Exemplary molecular sieves include silicas, metalloaluminates, aluminophosphates and gallogerminates, such as those described, for example, in Szostak (*Molecular Sieves: Principles of Synthesis and Identification*, Van Nostrand Reinhold, New York, 1989). The silicas include titanosilicates and metallosilicates. The metallosilicates include aluminosilicates (zeolites), gallosilicates, chromosilicates, borosilicates, and ferrisilicates. The metalloaluminates include germaniumaluminates. The aluminophosphates include silicon-substituted aluminum phosphate (SAPO) molecular sieves; metal-incorporated aluminum phosphate (MeAPO) molecular sieves (wherein the metal can, for example, be Li, Be, B, Mg, Si, Ga, Ge, As, Ti, Mn, Fe, Co or Zn); metal silicoaluminophosphate (MeAPSO) molecular sieves as well as ElAPO molecular sieves (such as those described, for example, in EP 158,976 and EP 158,349); and ElAPSO molecular sieves (such as those described, for example, in EP 159,624).

A zeolite, as used herein, is in general a crystalline aluminosilicate with a framework based on an extensive three-dimensional network of oxygen ions, as described, for example, in Szostak, supra; and Breck (*Zeolite Molecular Sieves*, John Wiley & Sons, New York, 1974). Situated within the tetrahedral sites formed by the oxygen can be either a $Si^{4+}$ or $Al^{3+}$ ion. The $AlO_2^-$ tetrahedra in the structure determine the framework charge. This is balanced by cations that occupy nonframework positions. A representative empirical formula for a zeolite may be written as $M_{2/n}O \cdot Al_2O_3 \cdot xSiO_2 \cdot yH_2O$, wherein "M" represents the exchangeable cations, generally from the Group I or II ions, although other metal, non-metal or organic cations may be used to balance the framework charge; and "n" represents the cation valence. These cations are present either during synthesis or through post-synthesis ion exchange. The value of "x" is equal to or greater than 2 because $Al^{3+}$ does not occupy adjacent tetrahedral sites. The pore or channel openings range from about 3 Å to greater than 7 Å, with the exact pore size dependent on the structure. Any water molecules present are located in these channels and cavities, as are the cations that neutralize the negative charge created by the presence of $AlO_2^-$ tetrahedral in the structure. Typical cations include alkaline cations such as $Na^+$, $K^+$, $Rb^+$ and $Cs^+$; alkaline earth cations such as $Mg^{++}$ and $Ca^{++}$; $NH_4^+$; and tetramethylammonium cations.

Suitable molecular sieves can be small-, medium-, or large-pore molecular sieves, or combinations thereof, and can include 3A (wherein 3A is a potassium-exchanged form of zeolite A), 4A or 5A in powder, bead or rod form (available from Sigma-Aldrich, St. Louis, Mo.); silicalite (available from Sigma-Aldrich); ETS-4 (titanium silicate, available from BASF, Florham Park, N.J.); and CG-180 MAP (available from Ineos, Joliet, Ill.).

A molecular sieve as used herein to convert trans-cis nepetalactone to cis-trans nepetalactone may have a pH in water of about 9 or higher, and more particularly about 10 or higher.

Both trans-cis nepetalactone and cis-trans nepetalactone convert to nepetalic acid in the presence of water. Nepetalic acid is a compound having the formula:

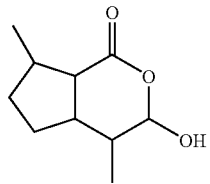

Thus, in one embodiment, molecular sieves as used herein include those that act as desiccants, i.e. that remove water present in trans-cis nepetalactone, or in a mixture of trans-cis nepetalactone and cis-trans nepetalactone. Examples of suitable desiccating molecular sieves include 3A, 4A and 5A.

In an alternative embodiment, however, to reduce the formation of nepetalic acid, trans-cis nepetalactone compound, or a T,C/C,T mixture, or catmint oil containing same, may be provided that contains less than about 0.3 wt % water by weight relative to the weight of the water and the compound or T,C/C,T mixture, or the weight of the water and the catmint oil. Where the compound, T,C/C,T mixture, or the catmint oil, contains more than about 0.3 wt % water, it may be desirable to select a dessicating molecular sieve such that less than about 5 wt % nepetalic acid is produced relative to the initial weight of nepetalic acid in the compound, T,C/C,T mixture or catmint oil. In addition, when water, ethanol or isopropyl alcohol is used as a solvent in the method, the use of a dessicating molecular sieve is recommended to reduce the formation of nepetalic acid.

Molecular sieves suitable for use herein can be obtained commercially, or can be prepared using methods known in the art. The molecular sieves employed herein may be used in the form of powders, granules or other particulate forms.

A molecular sieve for use herein may be any one or more of all the members of the total group of molecular sieves disclosed herein. The molecular sieve may also, however, be any one or more of those members of a subgroup of the total group of molecular sieves disclosed herein, where the subgroup is formed by excluding any one or more other members from the total group. As a result, the molecular sieve in such instance may not only be any one or more of the molecular sieves in any subgroup of any size that may be selected from the total group of molecular sieves in all the various different combinations of individual members of the total group, but the members in any subgroup may thus be selected and used in the absence of one or more of the members of the total group that have been excluded to form the subgroup. The subgroup formed by excluding various members from the total group of molecular sieves may, moreover, be an individual member of the total group such that that molecular sieve is used in the absence of all other members of the total group except the selected individual member.

It may be desirable to activate the molecular sieve(s) used herein by drying. Activation by heating may be carried out at a temperature of about 200° C. to about 500° C. or more in air, an inert gas, or under vacuum. Molecular sieve(s) are typically used in the method hereof in an amount such that the weight ratio of molecular sieve(s) to the trans-cis nepetalactone compound, T,C,/C,T mixture, or catmint oil containing same, is in the range of about 0.01/1 to about 5/1, or is in the range of about 0.01/1 to about 2/1.

Although there is no minimum length of time during which the molecular sieve(s) used herein are to be contacted with the trans-cis nepetalactone compound or T,C/C,T mixture—a period of one hour frequently being sufficient—it may be desirable to employ different periods of contact that are greater or less than one, including a relatively extended period of contact, such as a period of several hours, a period of several days, a period of a week or more, or even a period of several weeks. In general, the longer the period of contact, the more complete is the conversion of trans-cis nepetalactone to cis-trans nepetalactone.

There is similarly relatively wide latitude in choosing the temperature at which the trans-cis nepetalactone compound or T,C/C,T mixture is contacted with molecular sieve(s). A temperature in the range of about 20° C. to about 75° C., or in the range of about 50° C. to about 60° C., is generally found suitable. Where the T,C/C,T mixture is contained in catmint oil, a temperature up to the flash point of the catmint oil, which is frequently in the range of about 85° C. to about 95° C. at atmospheric pressure, may be used. The temperature at which contact occurs can be maintained constant, can be varied according to a pre-selected regime, or can be permitted to fluctuate without control.

The method of this invention may be carried out in batch in a single container opened or unopened to the atmosphere, or in a container under a blanket of an inert gas such as argon or nitrogen. Contact of the compound or T,C/C,T mixture with molecular sieve(s) can be carried out with or without stirring, as desired.

By the method hereof, about 50%, or about 60%, or about 70%, or about 80%, or about 90%, or about 99% of the trans-cis nepetalactone (by weight relative to the initial weight of the trans-cis nepetalactone present or in the T,C/C,T mixture) is converted to cis-trans nepetalactone.

After the T,C,/C,T mixture has been contacted with molecular sieve(s) for a period of time, and at a temperature, such that the desired extent of conversion has been obtained, the trans-cis nepetalactone compound or T,C,/C,T mixture, or the catmint oil containing same, may optionally be separated from the molecular sieve(s), and the molecular sieve(s) and/or products can be recovered. Suitable methods of separation, such as decantation and filtration, are known in the art. Following separation, the molecular sieve(s) can be recycled for further use in the method. For further use, it may be desirable to first re-activate the molecular sieve(s) by heating.

Where the treated trans-cis nepetalactone compound or the T,C/C,T mixture is contained in catmint oil, it may optionally then be hydrogenated to produce hydrogenated catmint oil, such as by the method disclosed in U.S. Provisional Application No. 60/876,568, which is by this reference incorporated in its entirety as a part hereof for all purposes. Where the treated trans-cis nepetalactone compound or the T,C/C,T mixture is not contained in catmint oil, or where cis-trans nepetalactone is recovered from treated catmint oil, the cis-trans nepetalactone may optionally then be hydrogenated to produce dihydronepetalactone by a method such as discussed above, including particularly the method disclosed in U.S. Pat. No. 7,067,677, which is by this reference incorporated in its entirety as a part hereof for all purposes.

The following examples are presented to illustrate the advantages of the present invention and to assist one of ordinary skill in making and using the same. These examples are not intended in any way to limit the scope of the disclosure, or the appended claims or equivalents thereof.

EXAMPLES

The following abbreviations are used: GC is gas chromatography; GC-MS is gas chromatography-mass spectrometry; FID is flame ionization detector; C is Centigrade; mL is milliliter; CMO is catmint oil; wt % is weight percent; NL is nepetalactone; c,t-NL is cis-trans nepetalactone; t,c-NL is trans-cis nepetalactone; NL3 is cis-cis nepetalactone; h or hr is hour; conc. is concentration; temp. is temperature; press. is pressure; ° C. is degrees Centigrade; g is gram; and RT is room temperature (about 25° C.).

SSO refers to Specialty Seeds of Oregon (Culver, Oreg.); Thacker refers to catmint oil (obtained by steam distillation of catmint plant material) supplied by George Thacker Sons (Alberta, Canada); AMT refers to catmint oil (also obtained by steam distillation) supplied by AM Todd & Co., Kalamazoo, Mich.; AMT SSO is catmint oil produced from SSO seeds by AM Todd & Co.; and Thacker SSO is catmint oil produced from SSO seeds by George Thacker Sons.

The composition of Thacker SSO and AMT SSO are shown in Table 1, wherein the distribution of the nepetalactone isomers in catmint oil from several sources was determined. The values for weight percent were calculated relative to the total CMO weight.

TABLE 1

| | Composition of untreated catmint oil | | | | |
|---|---|---|---|---|---|
| Oil | c,t-NL (wt %) | t,c-NL (wt %) | NL3 (wt %) | Total NL (wt %) | Nepetalic acid (wt %) |
| Thacker SSO | 17.7 | 47.5 | 1.1 | 66.3 | 3.3 |
| AMT SSO | 39.1 | 42.7 | 0.9 | 82.7 | 0.9 |

The following molecular sieves, as used in these examples, were obtained from the following manufacturers:

3A beads: 8-12 mesh, EMD Sciences (Gibbstown, N.J.);
3A powder: undried, Sigma-Aldrich (St. Louis, Mo.) Catalog #233641;
4A beads: 8-12 mesh, Davison Molecular Sieves (WR Grace, Columbia, Md.);
4A rods: Fluka (available from Sigma-Aldrich);
4A-b: 4A rods obtained from an unidentified source;
4A powder: 5 microns, Sigma-Aldrich;
5A: beads, 8-12 mesh, EMD Sciences;
13x: Two types:
13x-A: beads, 4-8 mesh, Sigma-Aldrich Catalog #208639;
13x-B: beads, 8-12 mesh, Sigma-Aldrich Catalog #208647;
H-Mordenite: ZEOLYST ZD 96065 (Calcined CBV-30A), Zeolyst Intl. (Valley Forge, Pa.);
Na-Mordenite: CONTEKA (now part of Zeolyst Intl.); CBV-10A, granulated to −10/+20 mesh;
H-ZSM-5: CU Chemie Uetikon GmbH (Hillsborough, N.J.), AG PZ-2/50H;
Na-ZSM-5: CU Chemie Uetikon AG, PZ-2/40 Na Calcined;
LSX: hydrated, United Catalyst, Inc., KY (8×12 beads);
Silicalite: ABSCENTS T-3000, powder, zeolite-Sigma-Aldrich Catalog #419095, Lot 04815 PF;
CG-180 MAP: zeolite of the type P, Crosfield (now part of INEOS Silicas (Lyndhurst, UK));
ETS4: ETS-4 is a small pore member of the Engelhard TitanoSilicate (ETS) family of mixed octahedral/tetrahedral microporous framework materials, which can be obtained from BASF (Florham Park, N.J.); and
EZ-500: ferrierite zeolite, Engelhard (now part of BASF) EZ-500.

Cs,Na—X was prepared as follows: Cesium impregnated Na—X, zeolite; NaX (5 g) (Alfa Aesar, Catalog #87950, —600 mesh) that was granulated to −20/+40 mesh was added to a solution containing 0.15 g of $CsNO_3$ (Sigma-Aldrich) in 3 g of distilled/deionized (DI) water. DI water (1.9 g) was slowly added to the mixture with stirring until incipient wetness was obtained. The sample was then dried at 70° C. in a vacuum oven.

The molecular sieves (also referred to herein as "sieves") were heated as described below to activate them. Heating of the molecular sieves was carried out using Method A, Method B, or as indicated in a particular example. According to Method A, activation of molecular sieves was carried out by heating in a vacuum oven held at 150° C. and 20 psig (137.9 kPa) of vacuum for 1 day under a constant flow of $N_2$. Following activation, the oven pressure was increased to room pressure and vials with the sieves were removed from the oven and capped. Molecular sieves were cooled to room temperature prior to use.

According to Method B, molecular sieves were inserted into a tube furnace designed for activating molecular sieves. A flow of nitrogen was passed through the tube and the inside of the tube containing the sieves was heated up to a fixed temperature as indicated in the various examples. This temperature was selected generally with reference to parameters recommended for each sieve by the manufacturer. The tube was then cooled down to room temperature under nitrogen. The sieves were then removed from the oven, placed in individual vials, and the vials were capped under air. Molecular sieves were cooled to room temperature prior to use.

Determination of Catmint Oil Constituents:

Samples of catmint oil were diluted with an internal standard solution and injected on a DB FFAP column using an HP5890 (Agilent Technologies, Palo Alto, Calif.) GC equipped with a FID detector. The injection and detector temperatures were 250° C. The temperature of the column was linearly ramped from 50° C. to 250° C. for 20 minutes, and held at 250° C. for the duration of the run. A split mode inlet was used. Peak identification and relative response factors of the major components were determined using calibration standards.

Contact of Molecular Sieves with Catmint Oil:

Mixtures of 1 g of catmint oil and 0.5 g of molecular sieve (unless indicated otherwise in an example) were prepared in 4 mL vials. The caps were closed under a selected atmosphere (for example, air or nitrogen) as indicated in the example, and the vials were incubated in ovens set at the temperature indicated. The weight percent of cis-trans nepetalactone and trans-cis nepetalactone relative to the total weight of nepetalactone was determined.

Example 1

Conversion with 4A Sieves (Rods)

This example shows the effect of molecular sieves (4A rods) and storage (i.e., contact or incubation) time on the conversion of t,c-NL to c,t-NL using Thacker SSO or AMT SSO. The molecular sieves (abbreviated "mol. sieve" in Table 2) were activated by Method A and the oils were stored in contact with the molecular sieve for one week at 35° C. or 55° C. More complete conversion of t,c-NL to c,t-NL was observed by storage at 55° C. The composition of the controls was taken from Table 1. The results are shown in Table 2, wherein the values for weight percent were calculated relative to the total CMO weight.

TABLE 2

| Oil | | c,t-NL (wt %) | t,c-NL (wt %) | NL3 (wt %) | Total NL (wt %) | Nepetalic acid (wt %) |
|---|---|---|---|---|---|---|
| Thacker SSO | Control | 17.7 | 47.5 | 1.1 | 66.3 | 3.3 |
| Thacker SSO | 35° C. + mol. sieve | 24.7 | 42.3 | 1.1 | 68.1 | 2.7 |
| Thacker SSO | 55° C. + mol. sieve | 64.0 | 1.5 | 1.1 | 76.5 | 1.9 |
| Thacker SSO | 55° C. - no mol. sieve | 18.8 | 46.7 | 1.1 | 65.9 | 3.9 |
| AMT SSO | Control | 39.1 | 42.7 | 0.9 | 82.7 | 3.6 |
| AMT SSO | 35° C. + mol. sieve | 52.3 | 25.8 | 0.9 | 79.0 | 2.0 |
| AMT SSO | 55° C. + mol. sieve | 74.4 | 0.7 | 0.8 | 75.9 | 1.3 |

Example 2

Conversion with Other Molecular Sieves

This example shows the effect of various other molecular sieves and storage times on AMT SSO oils stored at 55° C. The molecular sieves were activated at 150° C. using the vacuum oven (Method A). The results are shown in Table 3, wherein the values for weight percent were calculated relative to the total CMO weight.

TABLE 3

| Oil | Type of sieve | Days of storage | c,t-NL (wt %) | t,c-NL (wt %) | NL3 (wt %) | Total NL (wt %) |
|---|---|---|---|---|---|---|
| AMT SSO | 3A beads | 2 days | 38.0 | 39.0 | 0.8 | 77.8 |
| AMT SSO | 5A | 2 days | 33.7 | 39.7 | 0.8 | 74.2 |
| AMT SSO | 13x-A | 2 days | 41.8 | 40.4 | 0.9 | 83.1 |
| AMT SSO | 3A beads | 9 days | 43.2 | 28.8 | 0.8 | 72.8 |
| AMT SSO | 5A | 9 days | 34.0 | 39.2 | 0.8 | 74.0 |
| AMT SSO | 13X-A | 9 days | 48.0 | 29.2 | 0.8 | 78.0 |

Example 3

Conversion Activated at 250° C.

The sieves used in this example were activated at 250° C. using the tube furnace (Method B). The results are shown in Table 4, wherein the values for weight percent were calculated relative to the total CMO weight.

TABLE 4

| Oil | Type of sieve | Days of storage | c,t-NL (wt %) | t,c-NL (wt %) | NL3 (wt %) | Total NL (wt %) |
|---|---|---|---|---|---|---|
| AMT SSO | Control- 20° C. | 9 days | 36.2 | 43.0 | 0.9 | 80.1 |
| AMT SSO | Control- 55° C. | 9 days | 35.5 | 42.9 | 0.9 | 79.3 |
| AMT SSO | 3A beads- 55° C. | 9 days | 57.4 | 15.6 | 0.9 | 73.9 |
| AMT SSO | 4A-b rods- 55° C. | 9 days | 70.5 | 0.5 | 0.9 | 71.9 |
| AMT SSO | 4A rods - 55° C. | 9 days | 66.3 | 6.2 | 0.9 | 73.4 |
| AMT SSO | 4A beads- 55° C. | 9 days | 70.9 | 0.6 | 0.9 | 72.4 |
| AMT SSO | 5A- 55° C. | 9 days | 35.3 | 41.5 | 0.9 | 77.7 |
| AMT SSO | 13x-A- 55° C. | 9 days | 49.8 | 29.1 | 0.9 | 79.8 |

Example 4

Effect of Activation

AMT SSO was used, and the provided contact of sieves and CMO was carried out at 55° C. for 7 days. The sieves were heated (i.e. activated) at 250° C. using Method B, or not heated (i.e. not activated). Total NL was calculated as the sum of c,t-NL, t,c-NL, and NL3. NL3 data are not shown because these values did not appreciably change with incubation time. The results are shown in FIG. 1.

Example 5

Effect of Activation Temperature

Figure 2:
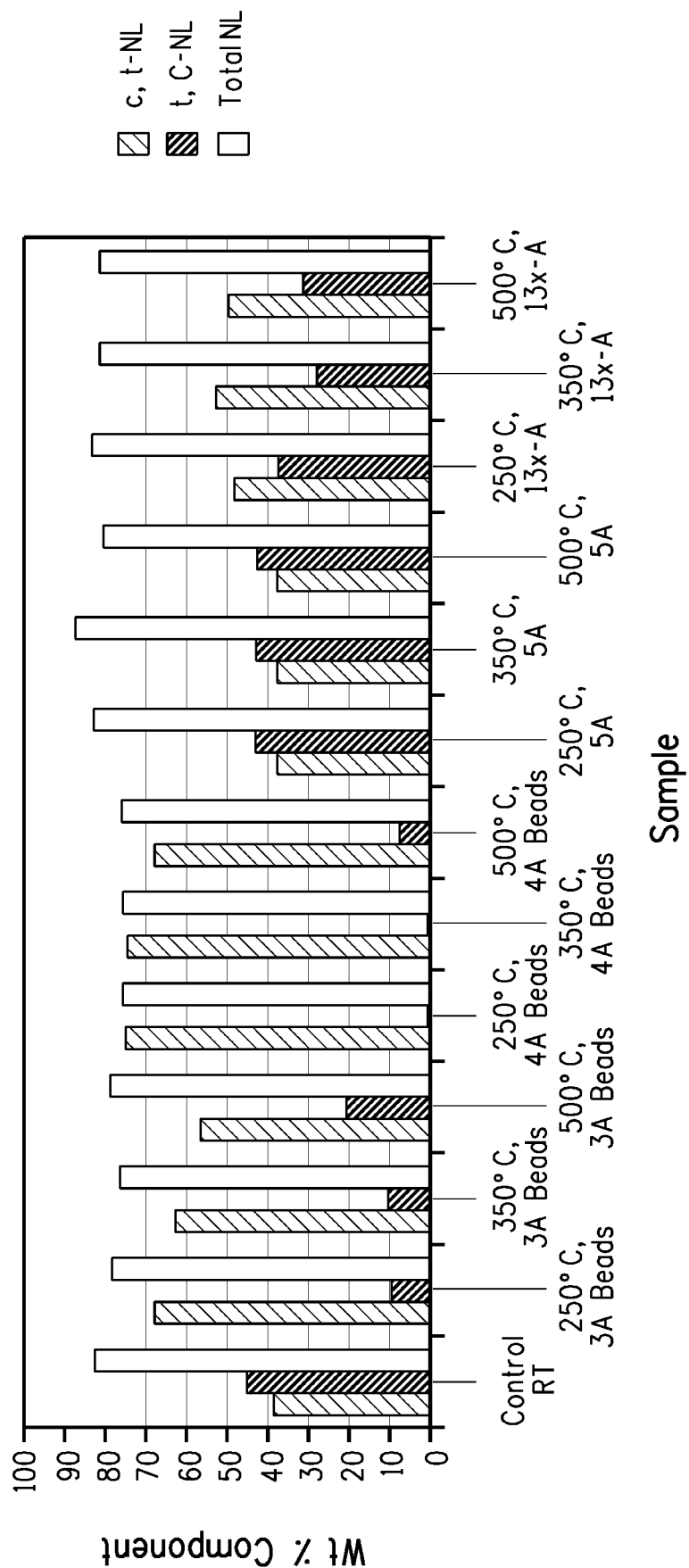
FIG. 2 shows the distribution of the trans-cis and cis-trans nepetalactone isomers after incubating catmint oil with molecular sieves activated at 250° C., 350° C. or 500° C.

The effect of molecular sieve activation temperature (250° C., 350° C. or 500° C. for 2 hrs) on AMT SSO was determined. The vials were incubated at 55-60° C. for 7 days. The results are shown in FIG. 2.

Example 6

Effect of Ratio of Sieves to Catmint Oil

Figure 3:
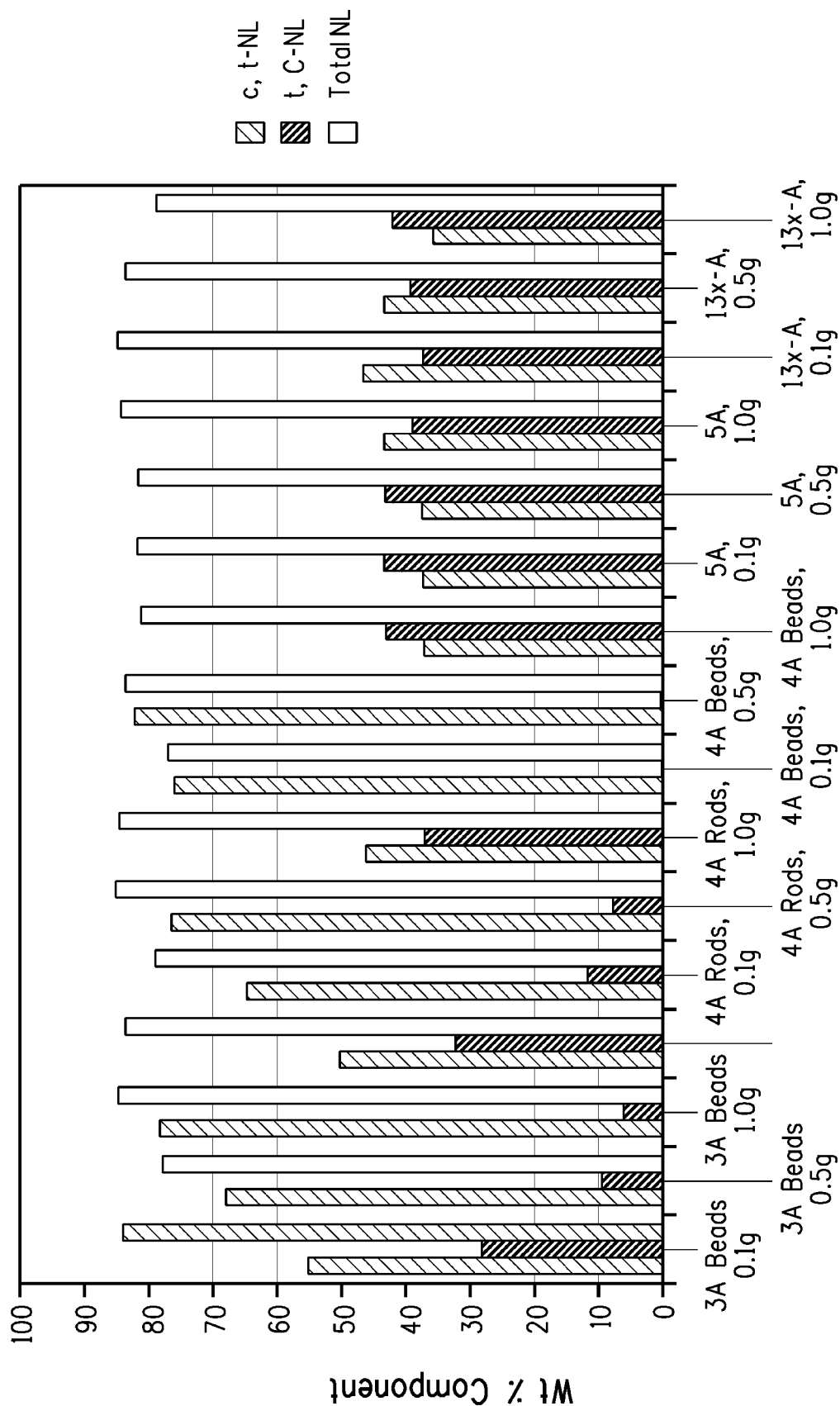
FIG. 3 shows the effect of varying the amount of molecular sieves on the conversion of trans-cis nepetalactone to cis-trans nepetalactone.

The molecular sieves were activated according to Method B. Mixtures of 1 g of catmint oil (AMT SSO oil) and increasing amounts of sieves (0.1 g, 0.5 g and 1 g) were prepared in 4 mL vials. The caps were closed and the vials were stored in an oven set at 55-60° C. for 7 days. The results are shown in FIG. 3.

Example 7

Effect of Gas Used During Storage

Figure 4:
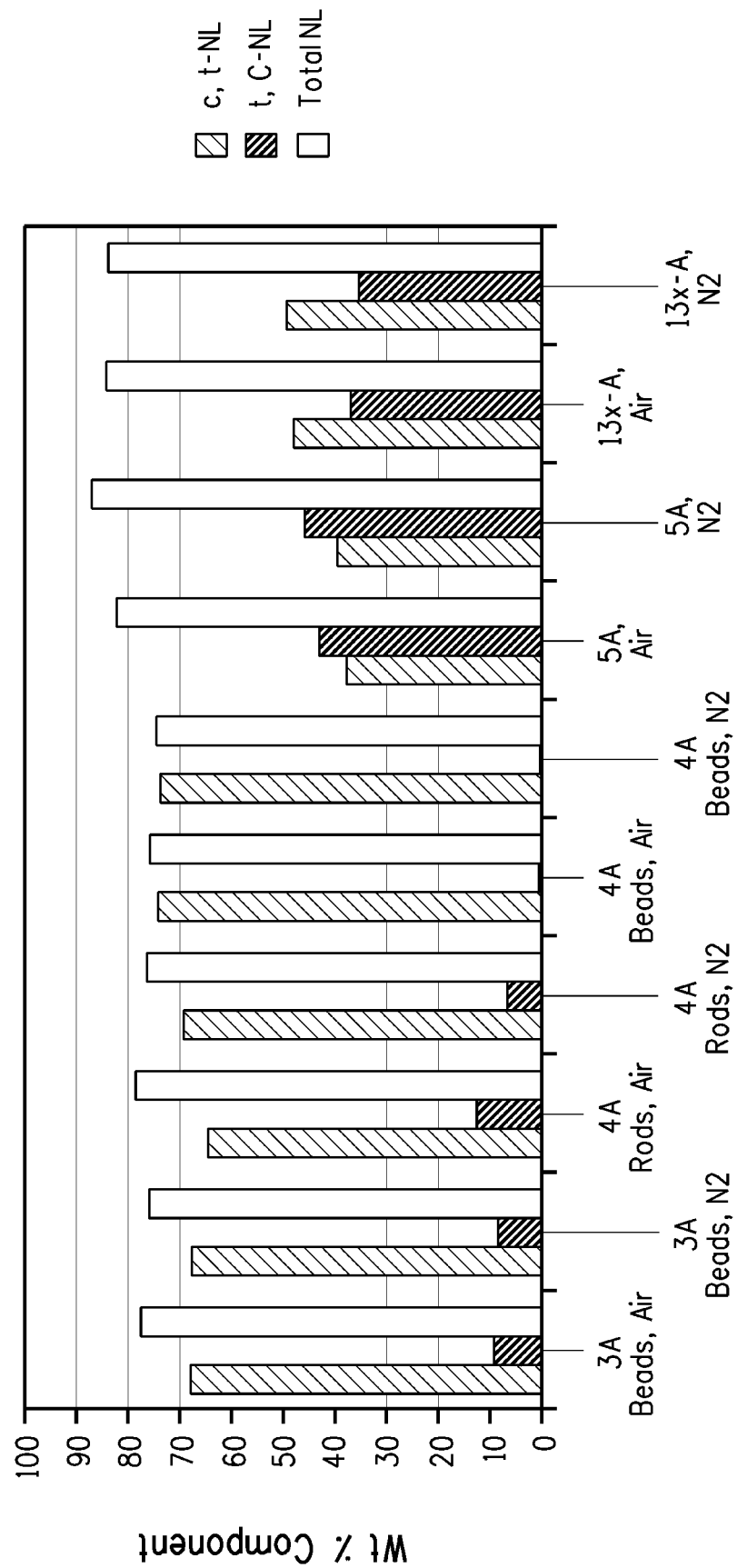
FIG. 4 shows the effect of a storage gas (air or nitrogen) on the conversion of trans-cis nepetalactone to cis-trans nepetalactone.

Molecular sieves were activated according to Method B. Mixtures of 1 g of catmint oil (AMT SSO oil) and 0.5 g of sieves were then prepared in 4 mL vials. The caps were closed and the vials were stored in an oven set at 55-60° C. for 7 days. Vials stored under nitrogen were sparged with nitrogen prior to closing the vials. The results are shown in FIG. 4.

Example 8

Effect of Recycling Molecular Sieves

Figure 5:
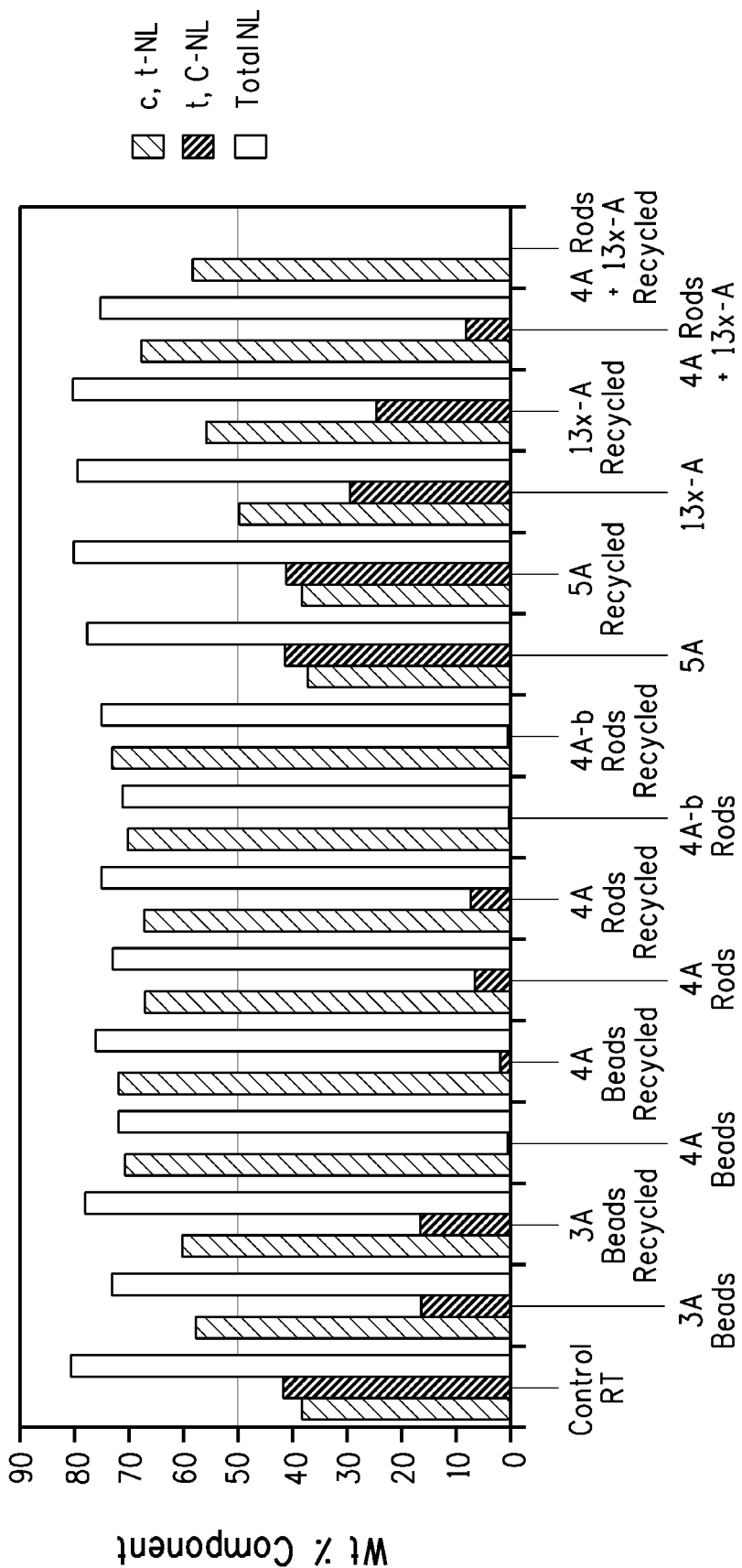
FIG. 5 shows the effect of recycling molecular sieves on the conversion of trans-cis nepetalactone to cis-trans nepetalactone.

Examples were prepared as described in Example 7 under air. After incubating for 7 days, the sieves were filtered from the CMO. The sieves were then heated inside a tube furnace at 350° C. to burn off the remaining catmint oil and regenerate them. Sieves were allowed to cool to room temperature. Mixtures of 1 g of catmint oil and 0.5 g of sieves were then prepared in 4 mL vials. The caps were closed and the vials were stored in an oven set at 55-60° C. for 7 days. The results are shown in FIG. 5.

Example 9

Effect of Various Molecular Sieves

Figure 6:
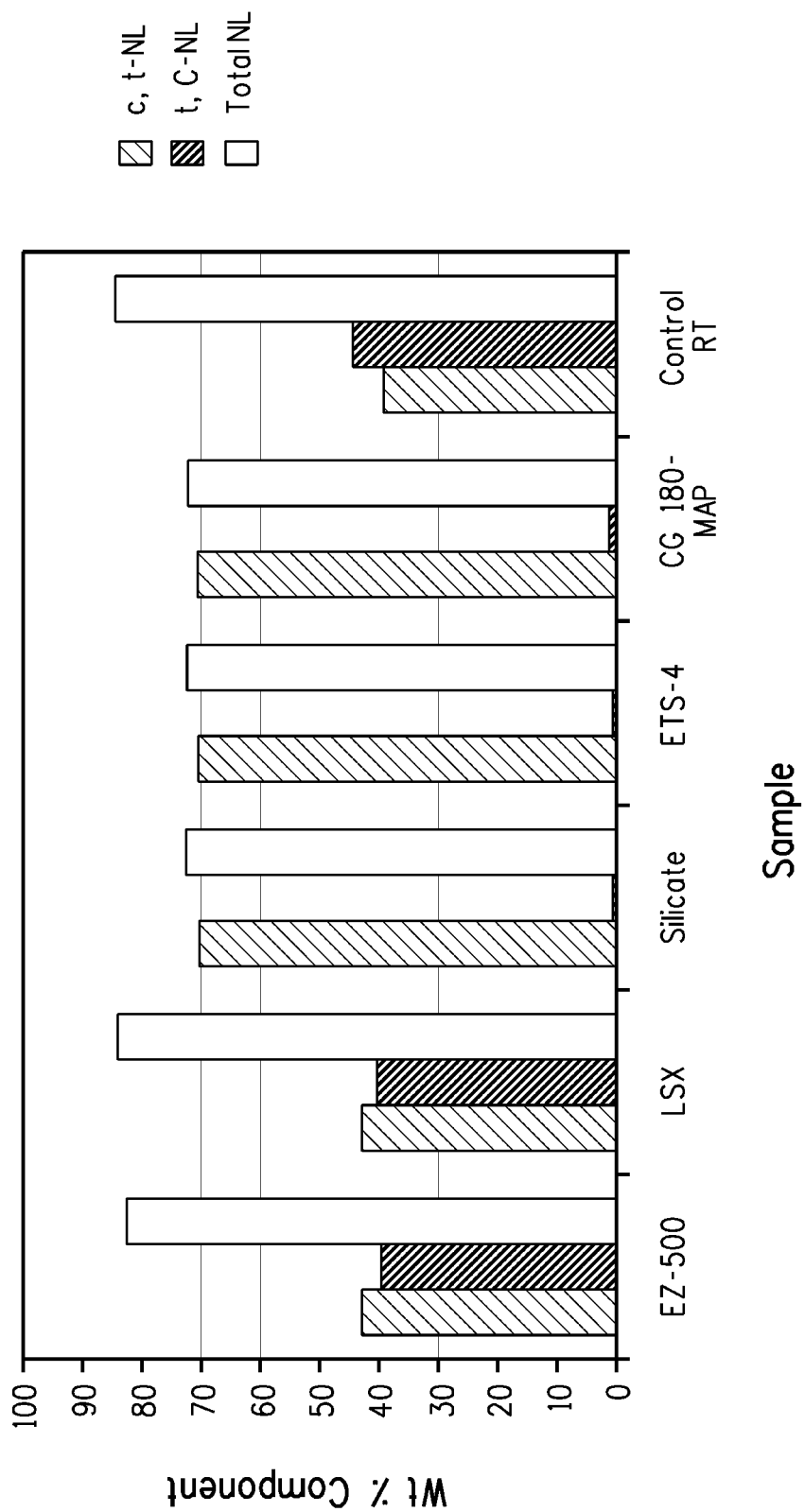
FIGS. 6 and 7 each shows the effect of various molecular sieves on the conversion of trans-cis nepetalactone to cis-trans nepetalactone.

The materials were treated by heating in a tube furnace at 350° C. for 2 hrs. Mixtures of 2 g of CMO and 0.5 g of each of the components were made and stored at 55-60° C. for a period of 1 week. The results are shown in FIG. 6.

Example 10

Effect of Various Molecular Sieves

Figure 7:
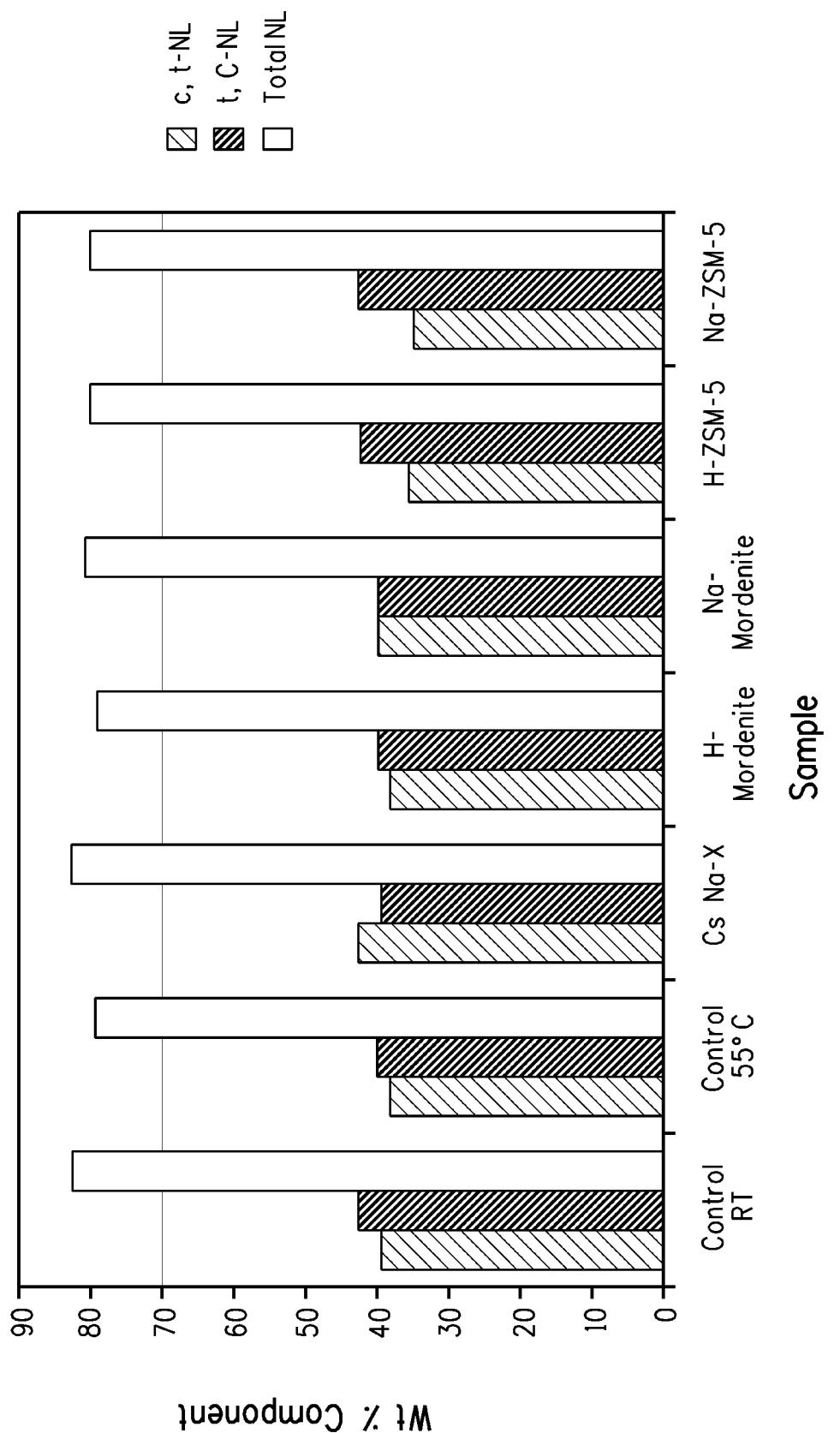

Cs,Na—X was treated by heating in a tube furnace at 350° C. for 2 hrs. All other materials were heated at 115° C. for 2 hrs. Mixtures of 2 g of CMO and 0.5 g of each of the molecular sieves were prepared and stored at 55-60° C. for a period of 1 week. The results are shown in FIG. 7.

Example 11 pH of Aqueous Solutions Containing Sieves

Figure 8:
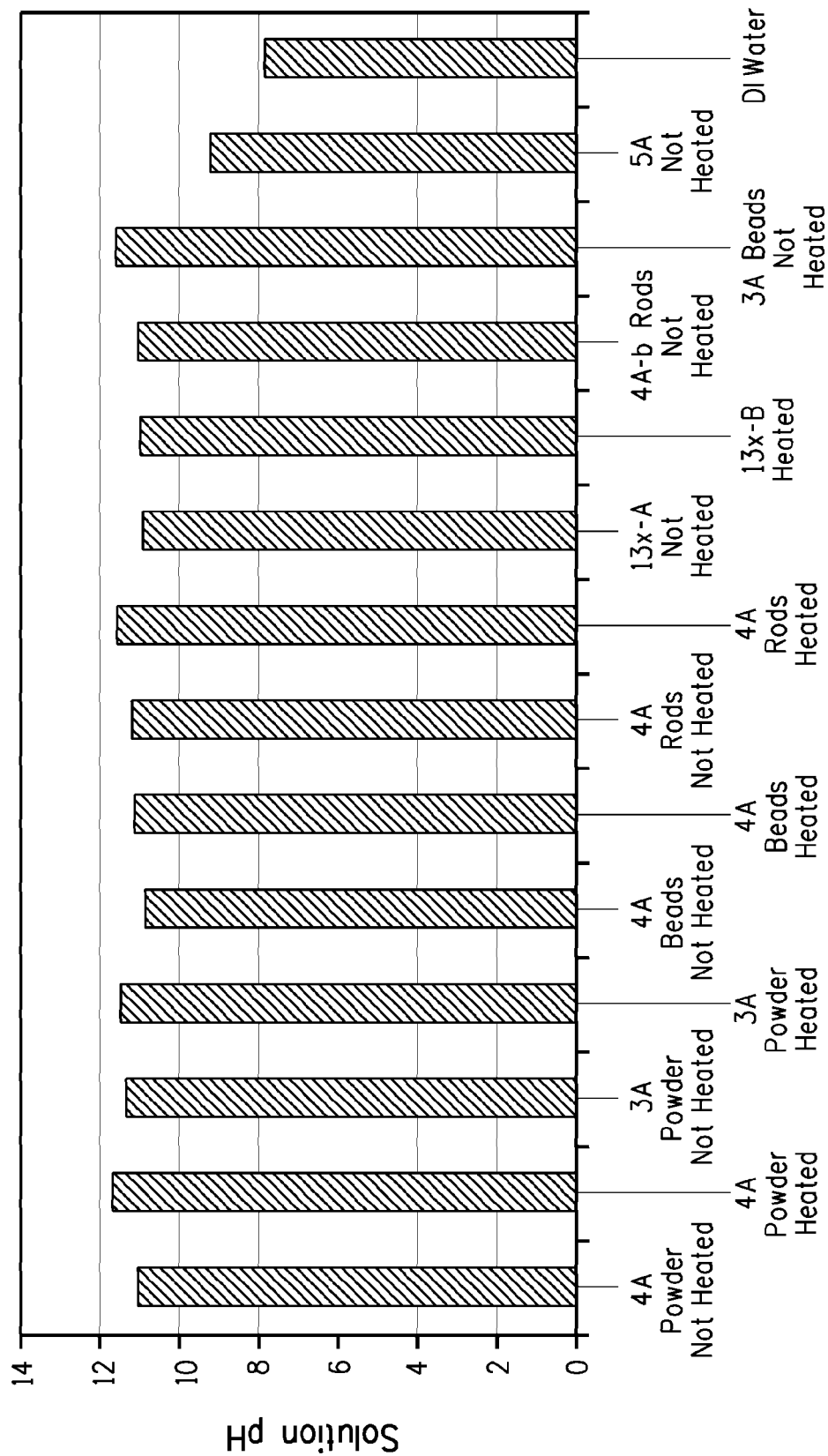
FIG. 8 shows the pH of various molecular sieves in water.

The pH of water containing molecular sieves was determined. The ratio of water to sieves was 2 to 1 (weight of water/weight of sieve). With heating, sieves slightly increased the pH of water. The results are shown in FIG. 8.

Example 12 pH of Aqueous Solutions Containing Sieves

Figure 9:
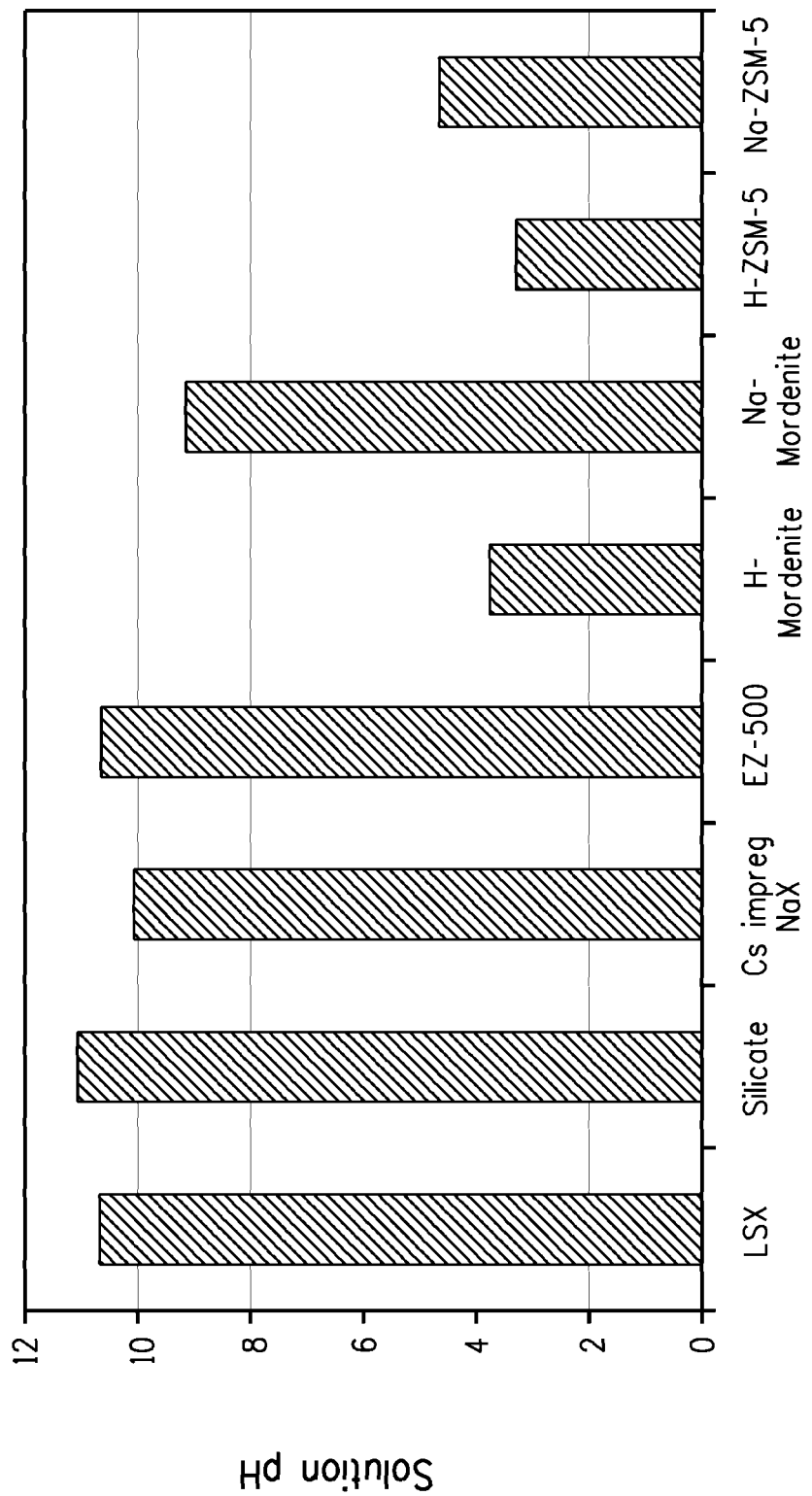
FIG. 9 shows the pH of various molecular sieves in water.

The pH of various molecular sieves in water was determined. The ratio of water to sieves was 2 to 1 (weight of water/weight of sieve). The results are shown in FIG. 9.

What is claimed is:

1. A method for converting trans-cis nepetalactone to cis-trans nepetalactone comprising contacting a trans-cis nepetalactone compound, or a mixture comprising trans-cis nepetalactone and cis-trans nepetalactone, with at least one molecular sieve, wherein a molecular sieve has a pH in water of at least about 8.

2. A method according to claim 1 wherein a molecular sieve has a pH in water of at least about 9.

3. A method according to claim 1 wherein a molecular sieve is selected from the group consisting of 3A, 4A, silicalite, CG 180-MAP and ETS-4.

4. A method according to claim 3 wherein a molecular sieve selected from the group consisting of 3A and 4A is further selected from a group consisting of powder, rods or beads.

5. A method according to claim 1 wherein the ratio of the weight of molecular sieve(s) to the weight of the trans-cis nepetalactone compound, or to the mixture comprising trans-cis nepetalactone and cis-trans nepetalactone, is in the range of about 0.01/1 to about 2/1.

6. A method according to claim 1 further comprising a step of heating a molecular sieve prior to contact with the trans-cis nepetalactone compound, or the mixture comprising trans-cis nepetalactone and cis-trans nepetalactone.

7. A method according to claim 1 wherein the trans-cis nepetalactone compound, or the mixture comprising trans-cis nepetalactone and cis-trans nepetalactone, is contacted with at least one molecular sieve for a period of at least about one hour.

8. A method according to claim 1 wherein the trans-cis nepetalactone compound, or the mixture comprising trans-cis nepetalactone and cis-trans nepetalactone, is contacted with at least one molecular sieve at a temperature in the range of from about 20° C. to about 75° C.

9. A method according to claim 1 wherein the trans-cis nepetalactone compound, or the mixture comprising trans-cis nepetalactone and cis-trans nepetalactone, is contained in catmint oil.

10. A method according to claim 1 wherein the trans-cis nepetalactone compound, or the mixture comprising trans-cis nepetalactone and cis-trans nepetalactone, is contained in catmint oil, and the catmint oil is contacted with at least one molecular sieve at a temperature that is less than or equal to the flash point of the catmint oil.

11. A method according to claim 1 wherein at least about 50 wt % by weight of the trans-cis nepetalactone compound, or at least about 50 wt % by weight of the trans-cis nepetalactone, relative to the initial weight of the trans-cis nepetalactone in the mixture, is converted to cis-trans nepetalactone.

12. A method according to claim 1 wherein the trans-cis nepetalactone compound, or the mixture comprising trans-cis nepetalactone and cis-trans nepetalactone, is contained in catmint oil; and, following conversion in the catmint oil of the trans-cis nepetalactone to cis-trans nepetalactone, the catmint oil is separated from a molecular sieve and recovered.

13. A method according to claim 12 wherein the recovered catmint oil is hydrogenated to produce hydrogenated catmint oil.

14. A method according to claim 1 wherein a mixture comprising trans-cis nepetalactone that has been converted to cis-trans nepetalactone, and trans-cis nepetalactone that has not been converted to cis-trans nepetalactone, is separated from a molecular sieve and recovered.

15. A method according to claim 14 wherein the recovered mixture is hydrogenated to produce dihydronepetalactone.

16. A method according to claim 1 wherein a molecular sieve is recovered and recycled for subsequent use.

17. A method according to claim 1 wherein the trans-cis nepetalactone compound, or the mixture comprising trans-cis nepetalactone and cis-trans nepetalactone, is derived from *Nepeta Cateria*.

18. A method according to claim 1 wherein a trans-cis nepetalactone compound is contacted with a molecular sieve.

19. A method according to claim 1 wherein a mixture comprising trans-cis nepetalactone and cis-trans nepetalactone is contacted with a molecular sieve.

20. A method according to claim 19 wherein (a) the mixture comprising trans-cis nepetalactone and cis-trans nepetalactone is contained in catmint oil; (b) following conversion in the catmint oil of trans-cis nepetalactone to cis-trans nepetalactone, the catmint oil is separated from a molecular sieve and recovered; and (c) the recovered catmint oil is hydrogenated to produce hydrogenated catmint oil.

* * * * *